United States Patent [19]

Moscatelli et al.

[11] Patent Number: 5,026,839
[45] Date of Patent: Jun. 25, 1991

[54] DNA ENCODING A BASIC FIBROBLAST GROWTH FACTOR

[75] Inventors: David A. Moscatelli; Daniel B. Rifkin, both of New York, N.Y.; Andreas Sommer, Boulder, Colo.

[73] Assignees: Synergen, Inc, Boulder, Colo.; New York University, N.Y.

[21] Appl. No.: 506,570

[22] Filed: Apr. 5, 1990

Related U.S. Application Data

[63] Continuation of Ser. No. 366,186, Jun. 14, 1989, abandoned, which is a continuation of Ser. No. 302,080, Jan. 26, 1989, abandoned, which is a continuation of Ser. No. 163,142, Feb. 24, 1988, abandoned, which is a continuation of Ser. No. 895,829, Aug. 12, 1986, abandoned, which is a continuation-in-part of Ser. No. 809,873, Dec. 17, 1985, abandoned.

[51] Int. Cl.$^5$ ............................................. C12N 15/018
[52] U.S. Cl. .................................... 536/27; 530/399; 435/69.4; 435/320.1
[58] Field of Search ........................ 536/27; 530/399; 435/69.4

[56] References Cited

U.S. PATENT DOCUMENTS

| | | |
|---|---|---|
| 4,209,587 | 6/1980 | Tolbert et al. |
| 4,529,590 | 7/1985 | LeVeen et al. |
| 4,956,455 | 9/1990 | Esch et al. ............................ 530/399 |

FOREIGN PATENT DOCUMENTS

| | | |
|---|---|---|
| 0061138 | 9/1982 | European Pat. Off. |
| 0275204 | 7/1988 | European Pat. Off. |
| 2146523 | 4/1985 | United Kingdom |
| WO86/07595 | 12/1986 | World Int. Prop. O. |
| WO87/01728 | 3/1987 | World Int. Prop. O. |

OTHER PUBLICATIONS

Bohlen, P. et al., FEBS Letters, vol. 185(1), 177–181 (6/85).
Young & Davis, Proc. Natl. Acad. Sci., vol. 80, 1194–1198 (3/83).
Suggs et al., Proc. Natl. Acad. Sci., vol. 78(11), 6613–6617 (11/81).
Gospodarowicz et al., Biochem. Biophys. Res. Comm., vol. 128(2), 554–562 (4/85).
Gospodarowicz et al., "Isolation of Brain Fibroblast Growth Factor . . . ", Proc. Natl. Acad. Sci., U.S.A., vol. 81, pp. 6963–6967 (11/84).
Bohlen et al., "Isolation and Partial Characterization . . . ", Proc. Natl. Acad. Sci., U.S.A., vol. 81, pp. 5364–5368 (9/84).
Gospodarowicz et al., "Fibroblast Growth Factor in Human Placenta", Biochem. Biophys. Res. Comm. (4/30/85).
Moscatelli et al., "Purification of a Factor from Human Placenta that Stimulates Capillary Endothelial Cell Protease Production, DNA Synthesis, and Migration", Proc. Natl. Acad. Sci. USA, 83: 2091–pp. 2095 (Apr. 1986).
J. W. Fett et al., "Isolation and Characterization of Angiogenin, An Angiogenin Protein from Human Carcinoma Cells," Biochemistry 24: 5486–5494 (Sep. 1985).
D. J. Strydom et al., "Amino Acid Sequence of Human Tumor Derived Angiogenin," Biochemistry 24:5486–5494 (Sep. 1985).
K. Kurachi et al., "Sequence of the cDNA and Gene for Angiogenin, a Human Angiogenesis Factor," Biochemistry 24:5497–5499, Sep. 1985).
Biological Abstracts, vol. 77, No. 3, 1984, p. 1911, Abstract No. 17462 to Burgos.
Chemical Abstract, vol. 103, No. 7, Aug. 1985, pp. 109–110, Abstract No. 48790e to Buki et al.
Biological Abstracts, vol. 81, No. 9, pp. AB-165, Abstract No. 79778 to Presta et al.

*Primary Examiner*—Margaret Moskowitz
*Assistant Examiner*—Nina Ossanna
*Attorney, Agent, or Firm*—Finnegan, Henderson, Farabow, Garrett & Dunner

[57] ABSTRACT

An isolated DNA sequence encoding an angiogenic factor protein consisting of a single-polypeptide-chain protein having at least one active site possessing mitotic and chemotactic activity and the ability to stimulate protease synthesis, wherein said protein consists of the amino acid sequence:

G—T—M—A—A—G—S—I—T—T—L—P—A—L—P—E—D—
—G—G—S—G—A—F—P—P—G—H—F—K—D—P—K—
—R—L—Y—C—K—N—G—G—F—F—L—R—I—H—P—D—
—G—R—V—D—G—V—R—E—K—S—D—P—H—I—K—L—
—Q—A—E—E—R—G—V—V—S—I—K—G—V—C—A—N—
—R—Y—L—A—M—K—E—D—G—R—L—L—A—S—K—C—
—V—T—D—E—C—F—F—F—E—R—L—E—S—N—N—Y—
—N—T—Y—R—S—R—K—Y—T—S—W—Y—V—A—L—K—
—R—T—G—Q—Y—K—L—G—S—K—T—G—P—G—Q—K—
—A—I—L—F—L—P—M—S—A—K—S.

In a preferred embodiment, the DNA sequence encodes basic fibroblast growth factor (bFGF).

1 Claim, No Drawings

DNA ENCODING A BASIC FIBROBLAST GROWTH FACTOR

This application is a continuation of application Ser. No. 366,186, filed June 14, 1989, abandoned, which is a continuation of U.S. Ser. No. 302,080, file Jan. 26, 1989, abandoned, which is a continuing application of U.S. Ser. No. 163,142, filed Feb. 24, 1988, and now abandoned, which is a continuation of Ser. No. 895,829, filed Aug. 12, 1986, which is now abandoned, which is a continuation-in-part of Ser. No. 809,873, filed Dec. 17, 1985, which is now abandoned.

BACKGROUND OF THE INVENTION

Angiogenic factors have been defined as proteins which possess a variety of properties, namely the ability to (1) increase the rate of endothelial cell proliferation; (2) increase endothelial cell protease synthesis; (3) stimulate endothelial cell migration toward the protein location; and (4) cause in vivo capillary proliferation. In particular, it has been observed that substances classified as angiogenic factors can be mitogenic by affecting DNA synthesis in endothelial cells, thus increasing the rate of endothelial cell proliferation and the rate at which new blood vessels are formed.

Interrelated with this property is the ability of angiogenic factors to increase protease synthesis by endothelial cells. The proteases include plasminogen activator (PA) and collagenase. Specifically, the angiogenic factor are able to stimulate synthesis of PA and latent collagenase where the PA can convert zymogen plasmin into active plasmin, a protease of wide specificity, which in turn can convert latent collagenase into active collagenase. These two proteases, active plasmin and active collagenase, are capable of degrading most of the proteins in surrounding tissues, thus allowing increased invasion of various tissues, such as capillary endothelial cells. Moreover, angiogenic factors are chemotactic for certain cells, particularly capillary endothelial cells, i.e. they induce these cells to migrate toward the angiogenic factor.

With these properties in mind, it has been postulated that the isolation of an angiogenic factor would allow creation of a therapeutic substance capable of increasing the blood supply to an organ. For instance, subsequent to certain myocardial infarctions it would be desirable to stimulate regeneration of the blood supply to the heart interrupted as a result of the infarction or to stimulate re-growth of vessels in chronic obstructions. In addition, the use of an angiogenic factor may stimulate healing in decubitus ulcers, surgical incisions and slowly healing wounds, particularly in geriatric and diabetic patients. Moreover, the application of this material to burns may improve the rate and degree of healing. Therefore, a purified angiogenic factor suitable for therapeutic applications in humans has been sought. Additionally, some scientists believe that study of a substance capable of stimulating blood vessel growth may lead to processes for which the blood supply to a cancerous tumor might be inhibited, thus starving the cancer.

Previously, although a class of proteins had been identified which have been referred to as "angiogenic factors," these proteins were primarily isolated from non-human sources. It is believed that angiogenic factors isolated from non-human sources would not be suitable for use as therapeutic agents in humans due to the potential for adverse immunological reaction in response to a foreign protein. Moreover, it has not been demonstrated whether these non-human proteins individually possessed the four identified properties of an angiogenic factor identified above or whether the observed properties were attributable to the interactions between a combination of proteins.

Indeed, various proteins which have been found to have endothelial cell mitogenic properties have been divided into two classes: endothelial cell growth factor-like molecules which are eluted from heparin-Sepharose with 1 M NaCl and which have an acidic pI; and fibroblast growth factor-like molecules which bind more strongly to heparin-Sepharose and which have a basic pI. In addition, the present inventors believe that there is a third species of angiogenic factor, that described as "angiogenin" in papers recently published by Vallee et al. of Harvard Medical School, in *Biochemistry*, 1985, Vol. 24, pgs. 5480–5499. It is believed that angiogenin, while possessing some properties of a true angiogenic factor, is a distinct species in that it lacks mitogenic properties.

In the face of this patchwork of research, the present inventors sought and discovered a human angiogenic factor, classifiable as an $FGF_{basic}$, which is substantially homologous to that isolatable from human placental tissue, which, in a single molecule, has the above-identified properties, i.e., is mitogenic, chemotactic, and capable of stimulating protease synthesis as well as capable of causing in vivo capillary proliferation. Furthermore, the present inventors sought to isolate this angiogenic factor in a substantially purified form from human placental tissues. The amino acid sequence of this isolated angiogenic factor has now been determined. It is believed that the determination of this amino acid sequence will allow identification of DNA probes for use in and obtaining genomic or cDNA sequences useful in recombinant-DNA methods for the synthesis of angiogenic factors.

SUMMARY OF THE INVENTION

The present invention relates to angiogenic factors generally, and more specifically, to those angiogenic factors classifiable as $FGF_{basic}$. In particularly, this invention relates to an $FGF_{basic}$ angiogenic factor which is substantially equivalent to that isolatable from human placental tissues, and which has mitogenic and chemotactic properties and which is capable of inducing protease synthesis and, in vivo, causes capillary proliferation.

An object of the present invention is to provide purified forms of an angiogenic factor which possess these properties. An additional object of the present invention is the determination of the amino acid sequence of such an angiogenic factor. A further object of the present invention includes providing purified forms of $FGF_{basic}$ which would be valuable as pharmaceutical preparations exhibiting mitogenic and chemotactic properties along with the ability to stimulate protease synthesis.

Additional objects and advantages of the invention will be set forth in the description which follows, and in part will be obvious from the description or may be learned from practice of the invention. These objects and advantages may be realized and attained by means of the instrumentalities and combinations particularly pointed out in the appended claims.

To achieve the objects and in accordance with the purposes of the present invention, an angiogenic factor is disclosed which has at least one active site possessing an activity selected from the group consisting of mitogenic activity, chemotactic activity, the ability to stimulate protease synthesis, and combinations thereof. The human or synthetic angiogenic factor is classifiable as an FGF$_{basic}$ and exhibits substantial homology to the native angiogenic factor isolatable from human placental tissue.

It should be noted that, while it is preferred that the angiogenic factor itself be capable of stimulating protease synthesis, the term "protease," as used herein, includes active or precursor forms. Examples of such precursor forms include latent or pro-collagenase. Moreover, it is possible that some angiogenic factors may be isolated that are encompassed within the scope of the present invention but which do not directly stimulate protease synthesis. These angiogenic factors, however, do cause biological responses which in turn stimulate protease synthesis. Thus, the angiogenic factors of the present invention either directly or indirectly stimulate protease synthesis.

A particularly preferred angiogenic factor according to the present invention has the following core amino acid sequence:

L—Y—C—K—N—G—G—F—F—L—R—I—H—P—D—G—R—

V—D—G—V—R—E—K—S—( )—P—H—I—K—L—Q—L—Q—

A—E—E—R—G—V—V—S—I—K—G—V—C—A—N—R—Y—

L—A—M—K—( )—D—G—( )—L—L—A—( )—K—( )—V—T—

( )—E—( )—F—F—F—E—( )—L—E—S—N—N—Y—N—T—

Y—R—( )—

In addition, peptides having the sequences

K—L—G—S—K—T—G—P—G—Q—K—A—I—L—F—

L—P—M—S—A—K and

Y—( )—S—W—Y—V—( )—L—( )

are present in the polypeptide outside the core sequence. In the sequences depicted herein, open parentheses indicate the presence of a single amino acid residue that is not completely identified. Another particularly preferred angiogenic factor has the following sequence:

G—T—M—A—A—G—S—I—T—T—L—P—A—L—P—E—D—
—G—G—S—G—A—F—P—P—G—H—F—K—D—P—K—
—R—L—Y—C—K—N—G—G—F—F—L—R—I—H—P—D—
—G—R—V—D—G—V—R—E—K—S—D—P—H—I—K—L—
—Q—A—E—E—R—G—V—V—S—I—K—G—V—C—A—N—
—R—Y—L—A—M—K—E—D—G—R—L—L—A—S—K—C—
—V—T—D—E—C—F—F—F—E—R—L—E—S—N—N—Y—
—N—T—Y—R—S—R—K—Y—T—S—W—Y—V—A—L—K—
—R—T—G—Q—Y—K—L—G—S—K—T—G—P—G—Q—K—
—A—I—L—F—L—P—M—S—A—K—S.

The amino acids represented by the foregoing abbreviations are set forth in the Description of the Preferred Embodiments below.

Furthermore, to achieve the objects and in accordance with the present invention, a substantially purified form of the native angiogenic factor isolatable from human placental tissue is disclosed. Additionally, to achieve the objects and accordance with the purposes of the present invention, pharmaceutical compositions containing, as at least one of the active ingredients, an angiogenic factor in accordance with the present invention as set forth herein are disclosed.

It is to be understood that both the foregoing general description and the following detailed description are exemplary and explanatory only and are not restrictive of the invention, as claimed.

DESCRIPTION OF THE PREFERRED EMBODIMENTS

References will now be made in detail to the presently preferred embodiments of the invention, which, together with the following examples, serve to explain the principles of the invention.

As noted above, the present invention relates to an angiogenic factor which has been isolated in purified form. Preferably, the angiogenic factor of the present invention is a single-polypeptide-chain protein which is substantially homologous to, immunologically equivalent to, and, most preferably, biologically equivalent to, native angiogenic factor isolatable from human placental tissues. By "biologically equivalent," as used throughout this specification and claims, it is meant that the composition of the present invention possesses mitogenic and chemotactic properties and is capable of inducing protease synthesis in the same manner, but not necessarily to the same degree, as the native angiogenic factor.

By "substantially homologous," as used throughout the ensuing specification and claims, is meant a degree of homology to the native angiogenic factor in excess of that displayed by any previously reported, purified, substantially homologous angiogenic factor composition. Preferably, the degree of homology is in excess of 50%, preferably 60%, and more preferably 75%, with particularly preferred proteins being in excess 85% or 90% homologous with the native protein. The degree of homology as described above is calculated as the percentage of amino acid residues found in the smaller of the two sequences that align with identical amino acid residues in the sequences being compared when four gaps in a length of 100 amino acids may be introduced to assist in that alignment as set forth by Dayhoff, M. O. in Atlas of Protein Sequences and Structure, Vol. 5, page 124 (1972), National Biochemical Research Foundation, Washington, D.C., specifically incorporated herein by references.

As described herein, the angiogenic factor of the present invention is either isolated from a human source or is a synthetic polypeptide. The term "synthetic" polypeptide is intended to mean an amino acid sequence which has not previously been isolated from nature in a substantially purified form. In applying this definition, "synthetic" encompasses, among others, polypeptides created by recombinant-DNA methods or synthesized in whole or in part in vivo. In particular, synthetic polypeptides are contemplated in which 1 or 2 amino acids differ from those set forth in the preferred sequences set forth below.

The preferred angiogenic factor of the present invention has been discovered in human placental tissue extracts and, for the first time, has been isolated in a purified form. For the purposes of the present application, "pure form" or "purified form," when used to refer to the angiogenic factor disclosed herein, shall mean substantially free of other proteins which are not angiogenic factors. Preferably, the angiogenic factor of the present invention is at least 50% pure, more preferably 70% pure and even more preferably 80% or 90% pure.

Additionally, the angiogenic factor of the present invention has been isolated from various tumor and normal cells. These include SK-Hep1 cells, HeLa cells and K562 cells, as well as human embryonic lung fibroblasts.

Isolation of this protein in a purified form was a prerequisite step to the correct sequencing of the protein and to the development of pharmaceutical compositions containing the angiogenic factor.

A preferred angiogenic factor of the present invention has the following core amino acid sequence:

L—Y—C—K—N—G—G—F—F—L—R—I—H—P—D—G—R—V—D—G—V—R—E—K—
S—( )—P—H—I—K—L—Q—L—Q—A—E—E—R—G—V—V—S—I—K—G—V—C—A—N—
R—Y—L—A—M—K—( )—D—G—( )—L—L—A—( )—K—( )—V—T—( )—E—( )—F—
F—F—E—( )—L—E—S—N—N—Y—N—T—Y—R—( )—

In addition, peptides having the sequences

K—L—G—S—K—T—G—P—G—Q—K—A—I—L—F—L—P—M—S—A—K and
Y—( )—S—W—Y—V—( )—L—( )

The angiogenic factor of the present invention may be isolated in pure form from human placental tissues by the method comprising: (a) collecting human placental tissues; (b) isolating the angiogenic factor from the human placental tissues by fractionating the proteinaceous material in the tissues; (c) identifying the fractions which possess angiogenic factor activity; and (d) concentrating the fractions exhibiting the angiogenic factor activity.

In a preferred embodiment, the proteinaceous material present in the human placental tissues is fractionated using a combination of heparin affinity chromatography, ion exchange chromatography and, optionally, gel permeation chromatography. The angiogenic factor discussed herein may also be isolated through the use of monoclonal antibodies with a specificity for the placental proteins. In this embodiment, antigen is bound to a matrix (resin) containing monoclonal antibodies against the placental protein and non-antigenic proteins are removed by washing the resin with buffer. The antigen is then removed from the antibody by the use of a buffer of either high or low pH, or high ionic strength, or chaotropic agents, alone or in combination with a change in temperature.

Fractions thus obtained are screened for the presence of angiogenic factor activity. Preferably, this is accomplished in part by evaluating the effect on PA and collagenase synthesis by incubating appropriate endothelial cell cultures, preferably mammalian capillary endothelial cells, in the presence of the angiogenic factor and assaying the medium for latent collagenase and the cells for PA. The amount of protease produced by the cells stimulated by the angiogenic factor may also be determined by immunological methods such as ELISA or RIA assays or immunoprecipitation methods.

The mitotic ability of the angiogenic factor is preferably measured by incubating appropriate endothelial cells, preferably mammalian capillary endothelial cells, in the presence of the angiogenic factor and a radiolabelled nucleotide, preferably $^{125}$I-iododeoxyuridine ($^{125}$I-dU). The amount of $^{125}$I-dU incorporated into trichloroacetic acid insoluble material is then measured as indicative of the extent of DNA synthesis. The chemotactic abilities of an angiogenic factor are preferably demonstrated by incubating an appropriate endothelial cell culture, preferably mammalian capillary endothelial cells, in the presence of the angiogenic factor and measuring cell motility in an appropriate vessel, preferably a modified Boyden chamber.

As noted above, the present inventors have succeeded in isolating an angiogenic factor from human placental tissues in a hitherto unavailable, purified form.

are present outside the core sequence. Another particularly preferred angiogenic factor has the following sequence:

G—T—M—A—A—G—S—I—T—T—L—P—A—L—P—E—D—
—G—G—S—G—A—F—P—P—G—H—F—K—D—P—K—
—R—L—Y—C—K—N—G—G—F—F—L—R—I—H—P—D—
—G—R—V—D—G—V—R—E—K—S—D—P—H—I—K—L—
—Q—A—E—E—R—G—V—V—S—I—K—G—V—C—A—N—
—R—Y—L—A—M—K—E—D—G—R—L—L—A—S—K—C—
—V—T—D—E—C—F—F—F—E—R—L—E—S—N—N—Y—
—N—T—Y—R—S—R—K—Y—T—S—W—Y—V—A—L—K—
—R—T—G—Q—Y—K—L—G—S—K—T—G—P—G—Q—K—
—A—I—L—F—L—P—M—S—A—K—S.

The foregoing abbreviations correspond to the standard abbreviations for amino acid residues as set forth in, for example, *Biochemistry* by A. L. Lehninger, 2nd, ed., Worth Publishers, Inc., New York (1975), pg. 72.

It is believed that the activity of the claimed angiogenic factors is not affected if any or all of the fifteen, sixteen, seventeen, or eighteen N-terminal amino acid residues are removed from the intact polypeptide. Thus, it is intended that all of these abbreviated sequences are encompassed in the present invention. Moreover, the extension of the amino acid sequence by the addition of up to 110 amino acids to the N-terminal amino acid of the intact polypeptide are also contemplated.

It is also contemplated that additions of polypeptide chains to the C- or N- terminus of the present angiogenic factor will be within the scope of the present invention. In particular, polypeptide chains may be joined to either terminus through protein fusion techniques. These additional polypeptides may serve to enhance the pharmacological efficacy of the instant angiogenic factors. For example, the polypeptide may, by fusion with other polypeptides, be made more capable of retaining its activity in the presence of low pH or high temperature, or the resultant polypeptide may possess a longer circulating life, greater resistance to degradation or increased ability to be transported across the intestinal epithelia.

However, it should be noted that, in these alterations, the variation to the amino acid sequences should not be such as to provoke an adverse immunological response in the organism to which the angiogenic factor is administered where such adverse response would be determined to be of such detriment to the organism that the benefits derived from the angiogenic factor would not be warranted. The methods of determining whether a biological molecule would provoke such an adverse immunological response are known to those of ordinary skill in the art.

The angiogenic factor of the present invention and its analogs as disclosed herein are contemplated for human and veterinary uses in the form of pharmaceutical products possessing mitogenic or chemotactic properties or having the ability to stimulate protease synthesis. It is expected that pharmaceutical preparations containing, as at least one of active ingredients, one of the present angiogenic factors would also contain appropriate, pharmaceutically acceptable carriers, diluents, fillers, binders and other excipients depending on the dosage form contemplated. For oral administration, steps must be taken to prevent degradation of the active protein in the digestive tract. Enteric coated dosage forms are thus contemplated as one form suitable for oral administration. If parental administration is chosen, the preparation may contain a water or saline solution or other pharmaceutically acceptable suspension agent. Generally, it would be preferred that a preparation intended for parenteral administration contain sodium chloride in sufficient concentrations to make the overall preparations isotonic to body fluids. It is also contemplated that the pharmaceutical preparations containing the angiogenic factor of the present invention be administered locally, as by injection or topical application, for treatment of wounds, surgical incisions or skin ulcers. Additionally, incorporation of the angiogenic factor into a slow release implant device is contemplated for administration to regenerate the blood supply to the heart after a myocardial infarction.

The calculations necessary to determine the appropriate dosage for treatment of each of the above-mentioned disorders and appropriate for use with the described delivery methods are routinely made by those of ordinary skill in the art and are within the ambit of tasks routinely performed by them without undue experimentation, especially in light of standard assays and the assays disclosed herein. These dosages may be ascertained through use of established assays for determining dosages utilized in conjunction with appropriate dose-response data.

It is understood that the application of the teachings of the present invention to a specific problem or environment will be within the capabilities of one having ordinary skill in the art in light of the teachings contained herein. Examples of the products of the present invention and representative processes for their isolation and manufacture appear in the following examples.

EXAMPLE 1

Purification of a Human Angiogenic Factor from Placenta Tissues

A. Protein Purification

Term human placentas were frozen at −20° C. after delivery. The frozen placentas were broken into small pieces, ground with an electric food chopper (General Slicing, Walden, N.Y.), and homogenized in a food processor. After homogenization, all subsequent steps were performed at 4° C. The homogenized placentas were diluted with cold 20 mM Tris, pH 7.5, 3 mM EDTA and were sonicated for 10 min. at 50 W (model 185 sonicator, Branson Sonic Power Co., Plainview, N.Y.). Generally, 1 kg of frozen placenta yielded 2 liters of sonicate.

The sonicate was brought to pH 4 with HCl, incubated at this pH for 2 min, followed by neutralization with NaOH. NaCl was added to a final concentration of 0.5 M and the sonicate was centrifuged at 10,000×g for 60 min. The supernatant was loaded on an 85×153 mm column of heparin-Sepharose (Pharmacia, Piscataway, N.J.) equilibrated with 0.5 M NaCl/3 mM EDTA/20 mM Tris, pH 7.5. The column was washed with the same buffer and was eluted with 2 M NaCl/3 mM EDTA/20 mM Tris, pH 7.5. The eluate was diluted with 3 mM EDTA/20 mM Tris, pH 7.5 until the conductivity was 24 mmho and loaded on a second heparin-Sepharose column (16×190 mm). The column was washed with 0.7 M NaCl in 3 mM EDTA/20 mM Tris, pH 7.5, and was eluted with a 0.7 to 2 M NaCl gradient in the same buffer.

Fractions were assayed for protease-inducing activity and the active fractions were concentrated on a third heparin-Sepharose column (12×75 mm). This column was washed first with 0.8 M NaCl in 3 mM EDTA/20 mM Tris, pH 7.5 and then with 0.2 M NaCl in 0.1 M sodium phosphate, pH 6.0 and was eluted with 2 M NaCl in 0.1 M sodium phosphate, pH 6.0. The active fractions from the third heparin-Sepharose column were diluted with 20-times their volume of 0.1 M sodium phosphate, pH 6.0.

The solution was clarified by centrifugation at 10,000×g for 30 min and was loaded on a 9×72 mm column of CM-Sephadex C-50 (Pharmacia) equilibrated with the same buffer. The column was sequentially eluted with 0.15, 0.5, and 2 M NaCl each in 0.1 M sodium phosphate, pH 6.0, and the fractions were assayed for protease-inducing activity.

The 0.5 M NaCl eluate of the CM-Sephadex column, which contained the protease-inducing activity, was concentrated on a 0.5 ml heparin-Sepharose column. This column was eluted with sequential 0.5 ml washes with 2 M NaCl in 60 mM sodium phosphate, pH 6.0. All activity was eluted in the first 1 ml. This eluate was run on an FPLC Superose-12 column (Pharmacia) in 2 M NaCl, 60 mM sodium phosphate, pH 6.0 with a flow rate of 0.5 ml/min.

An angiogenic factor within the scope of the present claims was isolated from this eluate. This angiogenic factor is referred to in part in this example as the "protein" or "proteins."

B. Characterization of Protein and Confirmation of Angiogenic Factor Properties

1. NaDodSO$_4$-PAGE

NaDodSO$_4$ polyacrylamide gels with 3% stacking gels and 10 to 18% gradient resolving gels were prepared and run according to the procedure of Laemmli as set forth in Nature 277: 680–685 (1970), specifically incorporated herein by reference. Proteins were detected with the silver stain procedure of Wray et al. as set forth in Anal. Biochem. 118: 197–203 (1981). The active fractions from this column contained a single band on NaDodSO$_4$-PAGE with a molecular weight of 18,700.

2. Protein determination

Protein concentrations were determined with the Bio-Rad protein assay (Bio-Rad Laboratories, Richmond, Calif.) using bovine serum albumin as a standard. The sequence information for this protein is set forth in Example 4.

3. Mitogenic Properties—$^{125}$I-iododeoxyuridine incorporation

Bovine capillary endothelial (BCE) cells were isolated from the adrenal cortex of recently slaughtered yearling cattle by the method of Folkman et al. as reported in Proc. Natl. Acad. Sci. U.S.A. 76: 5217–5221 (1979), specifically incorporated herein by reference. Cells were grown to confluence in alpha Minimal Essential Medium (MEM) containing 10% (v/v) calf serum and supplemented with medium conditioned by mouse sarcoma 180 cells as described by Gross et al. in J. Cell Biol. 95: 974–981 (1982), specifically incorporated herein by reference. When cultures reached confluence, the medium was changed to MEM containing 5% calf serum and no conditioning factors.

Confluent cultures of BCE cells were maintained in MEM with 5% calf serum for 7 days. The medium was then replaced with fresh MEM containing 5% calf serum and varying concentrations of purified placenta angiogenic factor. After 20 h, the medium was replaced with Dulbecco's Modified Eagle's medium containing 5% calf serum and 0.3 uCi/ml $^{125}$I-iododeoxyuridine (2000 Ci/mmole, New England Nuclear, Boston, Mass.). After a 16 h incubation in labelling medium, labelling was terminated by washing the cells with cold phosphate buffered saline. Incorporation of $^{125}$I-iododeoxyuridine into acid insoluble material was determined by incubating the cells in cold 5% trichloroacetic acid (TCA) for 30 min, washing twice with 5% TCA and distilled water. The TCA insoluble material was solubilized in 0.25 N NaOH and counted in a Packard 5210 gamma scintillation counter.

4. Migration assay

Migration assays were performed in 200 ul blind wells (Nucleopore, Pleasanton, Calif.) according to the method of Castellot as described in Proc. Natl. Acad. Sci. U.S.A. 79:5597–5601, specifically incorporated herein by reference, using 5 um pore size polycarbonate PVP-free filters precoated with gelatin and fibronectin. Ten-fold serial dilutions of the purified protease-inducing factor in MEM containing 0.5% fetal calf serum were placed in the bottom wells. The filters were then inserted and $5 \times 10^4$ BCE cells in 200 ul MEM with 0.5% fetal calf serum were added to the upper wells. After a 4 h incubation at 37° C., the medium in the upper wells was removed and cells on the upper surfaces of the filters were gently scraped off with a cotton swab. Then the filters were removed, dried at room temperature, and stained with Wright-Giemsa stain (Baker Chemical Co., Phillipsburg, N.J.). The total number of cells on the lower filter surface was counted under a light microscope (400X magnification).

5. Assays for the induction of PA and collagenase

Confluent cultures of BCE cells that had been maintained for at least two days in MEM containing 5% calf serum were changed to fresh MEM containing 5% calf serum and the substrate to be tested. After incubation at 37° C. for 24 h, the medium was collected from the cultures and was assayed for collagenase as described by Moscatelli et al. in Cell 20: 343–351 (1980), specifically incorporated herein by reference. All collagenase was in a latent form and was activated with trypsin to detect activity. The cell layers from these same cultures were washed twice with cold phosphate-buffered saline and were extracted with 0.5% (v/v) Triton X-100 in 0.1 M sodium phosphate, pH 8.1, and the cell extracts were assayed for PA activity as described by Gross et al., supra. Experiments have demonstrated that the amount of PA in cell extracts is proportional to the amount found in conditioned medium. One unit of protease-inducing activity was defined as the amount necessary to give half the maximal stimulation of PA and collagenase synthesis.

EXAMPLE 2

Purification of an angiogenic factor from Human Placental Tissue

The method of Example 1 was followed to obtain an eluate loaded onto the second heparin-Sepharose column. This column was washed with 0.95 M NaCl in 3 mM EDTA/20 mM Tris, pH 7.5, and was eluted with 2 M NaCl in the same buffer.

The 2 M eluate was dialyzed against 0.2 M NaCl/20 mM MES, pH 6.0. The dialysate was clarified by centrifugation at $100,000 \times g$ for 60 min. and was loaded on a Mono-S column in a Fast Protein Liquid Chromatography (FPLC) system. The column was washed with 0.2 M NaCl/20 mM MES, pH 6.0, and was eluted with a 0.2 to 2 M NaCl gradient in 20 mM MES, pH 6.0. Fractions were assayed for protease-inducing activity. The protease-inducing activity eluted at 0.45 to 0.6 M NaCl.

EXAMPLE 3

Purification of an Angiogenic Factor From Hepatoma Cells

All the purification steps, except the FPLC steps, were performed at 4° C. SK-Hep-1 cells (American Type Culture Collection (ATCC) Accession No. HTB 52) from confluent monolayers were scraped into cold PBS and pelleted by centrifugation at $400 \times g$ for 10 min. The cell pellet was suspended in 10 vol of PBS/0.5 M NaCl and sonicated for 3 min at 50 watts with a Branson Sonicator (Plainview, N.Y.). The extract was centrifuged ($10,000 \times g$, 1 h), and the supernatant was collected. The pellet was resuspended in 1 vol of PBS/0.5 M NaCl, sonicated and centrifuged.

The two supernatants were pooled and passed through a $28 \times 75$ mm column of heparin-Sepharose (Pharmacia, Piscataway, N.J.) equilibrated with PBS/0.5 M NaCl. The column was washed with 0.5 M NaCl/3 mM EDTA/100 mM Tris, pH 7.5 and eluted with a 0.5 to 2 M NaCl gradient in the same buffer. Fractions were assayed for PA-inducing activity, and the active fractions were pooled and diluted with 3 mM EDTA/20 mM Tris, pH 7.5 until the conductivity was 20 mmho.

The active material was then passed through a second heparin-Sepharose column ($10 \times 75$ mm) equilibrated with 0.5 M NaCl in 3 mM EDTA/20 mM Tris, pH 7.5. The column was washed first with 0.5 M NaCl and then with 0.9 M NaCl in 3 mM EDTA/20 mM Tris, pH 7.5, and was eluted with a 0.9 to 2 M NaCl gradient in the same buffer. The active fractions were concentrated on a third heparin-Sepharose column ($7 \times 85$ mm), which was washed with 0.5 M NaCl and then eluted with 2 M NaCl, both in 20 mM MES, pH 6.0. The active fractions from the third heparin-Sepharose column were diluted 1:10 with 20 mM MES, pH 6.0, and the solution was clarified by centrifugation at $100,000 \times g$ for 1 h.

The same was then loaded on a Mono-S FPLC column (Pharmacia) equilibrated with 0.2 M NaCl/20 mM MES, pH 6.0. The column was washes with 0.2 M NaCl and elution was achieved with a multilinear gradient of NaCl (0.2 to 2 M in 20 mM MES, pH 6.0). The fractions were assayed for PA-inducing activity and the active fractions were pooled and purity was determined by NaDod SO$_4$-PAGE.

EXAMPLE 4

The Determination of the amino acid sequence of placental angiogenesis factor (PAF) isolated from human placenta

A. LYS-C Peptides

Purified PAF in 20 mM MES, pH 6.0, 0.5 M NaCl was obtained by the method of Example 2, above. The native protein was subjected to digestion with endoproteinase Lys-C as follows: A reaction mixture containing 2 nmoles of native protein in 350 ul of 20 mM MES, pH 6.0, 0.5 M NaCl was adjusted to pH 8.7 by addition of 15 ul of 2 M NH$_4$HCO$_3$, pH 9.0, 1.17 units of endoproteinase Lys-C (Boehringer) was added and digestion was carried out at 37° C. for 7 hrs. and 30 min. 2-mercaptoethanol was then added to a final concentration of 1% (v/v) and incubation continued for 15 min. at 37° C. Trifluoroacetic acid (TFA) was added to a final concentration of 0.1% (v/v) prior to the fractionation of the digestion mixture by reverse phase high performance liquid chromatography (HPLC) using a Synchrom RP-8 column. The peptides were eluted from the column (flow rate 1.0 ml/min.) with 0.1% TFA in water (5 min.) followed by a linear gradient of acetonitrile made 0.1% in TFA (0–60% acetonitrile in 60 min.). The elution of peptides was monitored at A$_{215}$ and A$_{280}$ and appropriate fractions were collected manually.

A peptide eluting at 19% acetonitrile was sequenced by automated Edman degradation and gave the following sequence:

(K)—N—G—G—F—F—L—R—I—H—P—D—G—R—V—D—G—V—R—E—K

In this and following sequences, an amino acid residue depicted within parentheses is a residue which has not been unambiguously identified.

A peptide eluting at 19.8% acetonitrile was sequenced and gave the following result:

(K)—G—V—( )—A—N—( )—Y—L—(A)—M—K—(E)—D—G—

Another peptide from the same digest eluted at 17.5% acetonitrile and gave the following amino acid sequence:

(K)—L—Q—L—Q—A—E—E—R—G—V—V—S—I—K

A peptide that eluted at 26% acetonitrile was subjected to automated Edman degradation and gave the following amino acid sequence:

(K)—(C)—V—T—(D)—E—(C)—F—F—F—E—( )—L—E—S—N—N—Y—N—(T)—

Two additional peptides that eluted together at 16% acetonitrile were collected as a mixture and then repurified prior to sequencing. The collected peptide mixture was dried under vacuum, then resuspended in 100 ul of 50 mM Tris-HCl, pH 8.5, 8 M urea. Twenty nmoles of dithiothreitol (DTT) was added and the reduction of possible disulfide bonds was allowed to proceed for 15 min. at 37° C. The peptides were then carboxymethylated by addition of 60 nmoles of $^3$H-iodoacetic acid and the mixture was incubated for 20 min. in the dark at room temperature. An additional 60 nmoles of DTT was added followed by a 30 min. incubation at room temp. and the reaction mixture was adjusted to 0.1% in TFA prior to refractionation by HPLC using an Altex C-3 reverse phase column. The peptides were eluted (flow rate 1 ml/min.) from the column with 0.1% TFA in water (5 min.) followed by a linear gradient of acetonitrile made 0.1% in TFA (0–60% acetonitrile in 120 min.).

The peptide eluting at 13% acetonitrile was subjected to automated Edman degradation and gave the following sequence:

(K)—G—V—C—A—N—R—Y—L—A—M—K

B. SMP-Peptides

Additional peptides were generated by digestion of the native PAF protein with mouse submaxillary protease.

A solution containing 2 nmoles of protein in 350 ul of 20 mM MES, pH 6.0, 0.5 M NaCl was adjusted to pH 8.0 by addition of 25 ul of 1 M NaHCO$_3$, pH 9.0. Submaxillaris protease (3.6 ug) was added and the digestion was allowed to proceed for 24 hrs. at 37° C. 90 nmoles of DTT were added and the incubation at 37° C. continued for 30 min. Carboxymethylation of the peptides was achieved by the addition of 360 nmoles of $^3$H-iodoacetic acid and incubation at room temperature for 20 min. in the dark. 360 nmoles of DTT were then added and the reaction mixture was adjusted to 0.1% (v/v) in TFA prior to fractionation of the peptide mixture by RP-8 HPLC as described above.

A mixture of peptides eluting at 12% acetonitrile were collected in one fraction, dried down and resuspended in 100 ul of 50 mM Tris-HCL, pH 8.0, 8 M urea and then refractionated by HPLC using an Altex C-3 column and the same elution schedule as described above for the repurification of Lys-C peptides.

Two peptides eluting at (a) 14.8% acetonitrile and (b) 15.3% acetonitrile were subjected to automated Edman degradation and gave the following amino acid sequences:

(R)—G—V—V—( )—I—K—G—V—C—A—N—    (a)
(R)—L—V—C—K—N—G—G—F—F—    (b)

Several peptides were generated by digestion of the native PAF with *S. aureus* protease (V8). One nmole of protein in 500 ul of 20 mM Tris-HCl, pH 7.5, 2 M NaCl was desalted by HPLC using an RP-8 reverse phase column. The salt free, protein-containing fraction was dried down, resuspended in 50 ul of 50 mM acetic acid, pH 4.0 and 1 ug of V8 protease was added. Digestion was allowed to proceed for 18 hrs. at 37° C. Peptides were then fractionated by HPLC using an RP-8 reverse phase column as described above.

A peptide eluting at 17% acetonitrile was subjected to automated Edman degradation and gave the following amino acid sequence:

(E)—K—S—( )—P—H—I—K—L—Q—L—( )—A—E

An additional peptide from the V8 digest that eluted at 20% acetonitrile was also sequenced and gave the following result:

(E)—( )—(G)—( )—L—L—A—( )—K—

A V8 peptide eluting at 21% acetonitrile was sequenced with the following result:

(E)—S—N—N—Y—N—T—Y—R—(S)—

Ordering of all the amino acid sequences listed above leads to a core sequence for the human basic fibroblast growth factor as follows:

L—Y—C—K—N—G—G—F—F—L—R—I—H—P—D—G—R—V—D—G—V—R—E—K—
S—( )—P—H—I—K—L—Q—L—Q—A—E—E—R—G—V—V—S—I—K—G—V—C—A—N—
R—Y—L—A—M—K—( )—D—G—( )—L—L—A—( )—K—( )—V—T—( )—E—( )—F—
F—F—E—( )—L—E—S—N—N—Y—N—T—Y—R—( )—

Additional peptides were isolated and subjected to automated Edman degradation. These amino acid sequences are outside the core amino acid sequence listed above.

A peptide eluting at 13% acetonitrile upon fractionation of the submaxillaris digest (see above) gave the following amino acid sequence:

K—L—G—S—K—T—G—P—G—Q—K—A—I—L—F—L—P—M—S—A—K

A LYS-C peptide eluting at 20% acetonitrile gave the following amino acid sequence:

Y—( )—S—W—Y—V—( )—L—( )

EXAMPLE 5

Identification of Characteristics of the Angiogenic Factor that Make it Suitable for Clinical Use as Therapeutic Agent We have demonstrated that the factor from placenta, isolated by the method of Examples 1 or 2, and the factor isolated from hepatoma cells have all three of the in vitro properties predicted for an angiogenic factor. First, at concentrations in the range of 0.1 to 10 ng/ml, the molecule stimulates the synthesis of PA and latent collagenase in BCE cells. The PA can convert the zymogen plasminogen to active plasmin, a protease of wide specificity. The plasmin can also convert latent collagenase to active collagenase. Thus, under the influence of low concentrations of this factor, capillary endothelial cells can generate at least two proteases which are able to degrade most of the proteins in the surrounding tissues, which would allow the cells to penetrate the tissues.

The purified molecule stimulated PA and collagenase synthesis in BCE cells in a dose-dependent manner (FIG. 3A). All collagenase was in an inactive form. Collagenolytic activity was detected after trypsin treatment. Both PA and latent collagenase are stimulated in parallel. Half maximal stimulation occurred with a concentration of protease-inducing factor of 1 ng/ml. The basal amount of PA and collagenase produced by untreated cells varied from experiment to experiment, and, thus, the extent of stimulation also varied. With very high concentrations of the protease-inducing factor, the stimulation of PA synthesis was reduced as were the chemotactic and mitogenic activities. Incubation of BCE cells for 24 hours with concentrations of the protease inducing factor that induced PA and collagenase altered the morphology of the cells from their typical cobblestone appearance to a more elongated, spindle-shaped appearance.

Second, the factor is chemotactic for BCE cells. In vivo, capillary endothelial cells, therefore, would be stimulated to migrate toward the source of the factor. The addition of the factor at concentrations between 0.001 and 0.1 ng/ml stimulated BCE cell chemotaxis in blind well chambers. With higher concentrations, stimulation of chemotaxis did not occur. Increased cell movement from the upper chamber to the lower chamber was detected only when the lower chamber contained a higher concentration of factor than the upper chamber, demonstrating that true chemotaxis was occurring. Chemokinesis accounted for no more than 25% of the observed increased motility.

Third, the factor is mitogenic for BCE cells. FIG. 3B demonstrates that addition of the protease-inducing factor to cultures of BCE cells stimulated the incorporation of $^{125}$I-iododeoxyuridine into DNA in a dose-dependent manner. At higher concentrations of protease inducing factor, this stimulating effect was significantly reduced. Stimulation of $^{125}$I-iododeoxyuridine incorporation was achieved with the same concentrations of factor which were able to induce PA and collagenase. We have previously determined that, with crude placenta sonicate, increased incorporation of $^{125}$I-iododeoxyuridine into DNA correlates with other measurements of mitogenesis. Thus, this factor behaves as a bona fide endothelial cell mitogen. Thus, a single purified molecule seems to have the ability to induce PA and collagenase in BCE cells, to stimulate their replication, and to stimulate their motility.

EXAMPLE 6

Angiogensis Activity

Using the method of Dunn et al., as published in Anat. Rec. 199: 33–42 (1981), for determining angiogensis, the angiogensis factor of Example 2, when placed on a chick chorioallantoic membrane, stimulated angiogensis in 81% of the eggs at a dose of 65 ng.

EXAMPLE 7 a) N-Terminal Amino Acid Sequence of PAF

Human placental angiogenesis factor was purified as described previously (see Examples 1 and 2). The purified protein in 20 mM MES buffer, pH 6.0 and 500 mM NaCl was desalted by high performance liquid chromatography using an RP-8 reverse phase column. Two-hundred fifty to five hundred pmoles of desalted protein was applied to an ABI 470A gas-phase protein sequencer for automatic Edman degradation. The resulting PTH amino acids were identified by high performance liquid chromatography using a cyano reverse phase column.

These experiments resulted in the establishment of an N-terminal amino acid sequence for PAF as follows:

G—T—M—A—A—G—S—I—T—T—L—P—A—L—P—E

In addition, the N-terminal PAF amino acid sequence just described was also identified by automated Edman degradation of a Lys-C peptide that eluted at 23% acetonitrile in the chromatographic system described in Example 4, A.

b) C-Terminal Amino Acid Sequence of PAF

A C-terminal PAF peptide was isolated from the PAF Lys-C digest as described in Example 4. The peptide eluted at 22% acetonitrile. Automated Edman degradation of this peptide gave the following amino acid sequence:

A—I—L—F—L—P—M—S—A—K—S

Combining sequence data from (i) example 4; (ii) the N-terminal amino acid sequence of PAF; (iii) the C-terminal amino acid sequence of PAF; and (iv) cDNA, a complete amino acid sequence for PAF is as follows:

1. PAF form 1

G—T—M—A—A—G—S—I—T—T—L—P—A—L—P—E—D—
—G—G—S—G—A—F—P—P—G—H—F—K—D—P—K—
—R—L—Y—C—K—N—G—G—F—F—L—R—I—H—P—D—
—G—R—V—D—G—V—R—E—K—S—D—P—H—I—K—L—
—Q—A—E—E—R—G—V—V—S—I—K—G—V—C—A—N—
—R—Y—L—A—M—K—E—D—G—R—L—L—A—S—K—C—
—V—T—D—E—C—F—F—F—E—R—L—E—S—N—N—Y—
—N—T—Y—R—S—R—K—Y—T—S—W—Y—V—A—L—K—
—R—T—G—Q—Y—K—L—G—S—K—T—G—P—G—Q—K—
—A—I—L—F—L—P—M—S—A—K—S.

2. PAF form 2: N-terminally blocked PAF

From a number of experiments in which purified and intact PAF was subjected to automated Edman degradation, it became evident that a fraction of the applied protein (50-80%) is not degraded in the Edman procedure.

It is concluded that there exists a fraction of PAF protein molecules that are N-terminally blocked.

The nature of the blocking group is most clearly determined by the study of purified amino terminal PAF peptides. Amino terminal peptides from enzymatic degradations of PAF (see Example 4) are identified by amino acid analysis. They may also be identified by paper electrophoresis or thin layer chromatography followed by staining with the chlorine/o-tolidine reagent as described by (Reindel, F. and Hoppe, W. (1954) in Chem. Ber. 87, 1103-1107 specifically incorporated herein by reference. (Blocked peptides are not detected with nonhydrin (apart from a weak development of colour with the side-chains of lysine residues) unless first hydrolyzed.)

In addition, small, N-terminally blocked PAF peptides may be isolated by chromatography of acidified thermolysin or pepsin PAF digests on Dowex 50, X2 (H+ form) as described by Narita et al. (1975) in Protein Sequence Determination, pp. 30-103, Springer-Verlag, Berlin, Heidelberg, New York or by chromatography on Sulphoethyl-Sephadex as described by Kluh, I. (1979) in Coll. Czech. Chem. Comm. (Engl. Ed.), 44, 145-147, both of which are specifically incorporated herein by reference.

The structure of the short blocked peptides is determined by a variety of standard procedures and methods. For example, see Allen, G. (1981) in Sequencing of Proteins and Peptides; North Holland Publishing Company, Amsterdam, New York, Oxford or references discussed therein, which are specifically incorporated herein by reference. These procedures and methods included digestion of the N-terminally blocked peptides with carboxypeptidases, proglutamate aminopeptidase, hydrazinolysis, mass spectrometry, nuclear magnetic resonance spectrometry, gas chromatography, and fast-atom bombardment mass spectrometry as described by Boissel et al. (1985) Proc. Natl. Acad. Sci. U.S.A., 82, 8448-8452.

3. PAF form 3: Truncated and Extended PAF

It has been shown that bovine kidney fibroblast growth factor (FGF) lacks a number of amino acids from the N-terminus (Baird, A. et al. (1985); Regul. Pept; in press) (Gospodarowicz, D. (1986) Meth. Enzymol., in press). The truncated fibroblast growth factor retains its ability to bind to the FGF receptor, as shown by Neufeld, G. and Gospodarowicz, D. (1985) in J. Biol. Chem. 260, 13,860-13,868, indicating that the N-terminus of the protein does not play a crucial role in the interaction of FGF with its cell surface receptor. Therefore, is anticipated that both truncated and extended forms of PAF will retain receptor binding activity. The maximum N-terminal PAF deletion or extension that still allows for biological PAF activity remains to be determined.

EXAMPLE 8

A cDNA Clone of PAF

SK-HEP-1 cells were grown in Eagles Minimal Essential Media supplemented with 10% fetal calf serum, non-essential amino acids and Pen-Strep. RNA was isolated from cells using the NP-40 lysis procedure as described by Maniatis et al. in Molecular Cloning: A Laboratory Manual (Cold Spring Harbor Laboratory, New York, 1982, pg. 191-193), specifically incorporated herein by reference. Poly (A)+ mRNA was selected by oligo dT chromatography (BRL) using the procedure of H. Aviv and P. Leder described in Proc. Natl. Acad. Sci. U.S.A. 69, 1972, 1408 specifically incorporated herein by reference. Five ug of mRNA was used to synthesize 8 ug of double standard cDNA using oligo dT primed 1st strand synthesis and RNase H-DNA polymerase mediated 2nd synthesis as described by Gubler and Hoffman in Gene, 25 (1983) 263-269, specifically incorporated herein by reference. Amersham Reagents were used in this procedure. The following reactions, unless otherwise stated, were done according to manufacturers specifications. This cDNA was blunt ended using 10 using T4 DNA Polymerase (Amersham). EcoRI sites were protected with 400 units EcoRI methylase (New England Biolabs) and 100 mM S-adenosyl methionine. An equal mass amount of EcoRI linkers (New England Biolabs, 8 mer) were attached with 1 unit T4DNA ligase (Promega Biotec). Excess linkers were removed by digesting with 200 units EcoRI (New England Biolabs) and 100 ng of this cDNA was ligated into 1 ug of EcoRI-digested, alkaline phosphatase-treated lambda gt-10 DNA (Vector Cloning Systems). The DNA was the packaged in vitro (Vector Cloning Systems) and when plated on E. coli, C600 HFLa yielded $8.2 \times 10^5$ recombinants.

Design of Oligonucleotide Probes

Two mixed sequence oligonucleotide probes were used for the isolation of the SK-HEP-1 cDNA clone. The probes consist of pools of all possible DNA sequences for a given amino acid sequence. Probes were made to selected amino acid sequences in the core PAF amino acid sequence described in this application. Probe #5 was made to hybridize to DNA coding for the amino acid sequence Ile-Lys-Gly-Val-Cys-Ala, and is a 17-mer consisting of 192 sequences:

```
#5    Ile  Lys  Gly  Val  Cys  Ala
   5' ATZ  AAN  GGX  GTX  TGY  GC 3'
        192-fold degenerate, 17 mer
```

Code
X = A, T, G or C
N = A or G
Y = T or C
Z = T, C or A

Probe #8 was made to hybridize to DNA coding for the amino acid sequence Tyr-Cys-Lys-Asn-Gly-Gly-Phe, and is a 20 mer consisting of 256 sequences:

```
#8    Tyr  Cys  Lys  Asn  Gly  Gly  Phe
   5' TAY  TGY  AAN  AAY  GGX  GGX  TT 3'
           256-fold degenerate, 20 mer
```

Both probes were synthesized on an Applied Biosystems DNA synthesizer. They were gel purified and radiolabeled with [$\gamma$-$^{32}$p] ATP (Amersham) using T4 polynucleotide kinase (Pharmacia) to a specific activity of $4-6 \times 10^6$ cpm/pmol.

Hybridization temperatures were chosen to be 2° C. below the calculated Tm for the most AT-rich member of each pool as described by S. V. Suggs et al., (Developmental Biology Using Purified Genes (eds. D. D. Brown and C. F. Fox), 683–693 (1982) Academic Press, New York), specifically incorporated herein by reference. The final wash was done at the calculated Tm for the most AT-rich member of the pool (i.e., 2° C. above the hybridization temperature).

Screening

The cDNA library was plated at a density of 50,000 plaques per 150 mm Luria-Bertoni agar plate with *E. coli* C600 HFLa cells and NZCYM top agarose (0.7%). Phage DNA was transferred to duplicate nitrocellulose filters (Schleicher and Schuell, BA 85) and prepared for hybridization as described by Benton and Davis in Science, 196: (1979) 180–182, specifically incorporated herein by reference. The filters were prehybridized at 48° C. for 2 hours in a solution containing 6X SSC (20X SSC is 3 M NaCl, 0.3 M Sodium Citrate, pH 7.5), 2X Denhardts Solution (100X Denhardts Solution is 2% Ficoll, 2% Polyvinyl pyrrolidone and 2% BSA), 0.1% SDS, 0.05% Sodium Pyrophosphate and 100 mg/ml yeast tRNA. Probe #8 was added at 0.2 pmol/ml and allowed to hybridize for 16 hours. After hybridization, the filters were washed as follows: 3 times for 15 minutes each in 6X SSC and 0.1% SDS at ambient temperature followed by a final 8 minute wash at 50° C. The filters were then dried and autoradiographed for 24 hours on Kodak XAR5 film and one "lightening plus" intensifying screen at −70° C. Plaques giving positive signals on duplicate filters were picked for purification. Those plaques were tested with probes #5 and #8 in second round of purification and a plaque hybridizing to both probes was chosen as the best candidate to code for the angiogenesis factor.

DNA was prepared from this phage by plate lysates and formamide extraction as described by R. W. Davis, D. Botstein, and J. R. Roth in Advanced Bacterial Genetics: A Manual for Genetic Engineering (Cold Spring Harbor Laboratory, New York, 1980), specifically incorporated hereby in reference. An EcoRI digest of this DNA released a 1.1 kb insert as sized in 1% agarose gel. This insert was purified out of a 5% acrylamide gel for subcloning as described by Maniatis et al., supra at 173–178. The insert was ligated into EcoRI digested Bacteriophage M13 mp 19 RF DNA and its sequence was determined using the dideoxynucleotide method of Sanger et al. described in J. Mol. Biol. 94, 441 (1975), specifically incorporated herein by reference. Analysis of the sequence obtained showed an open reading frame encoding the primary structure of PAF.

Based on protein sequence data (see Example 7) and published FGF information (Esch et al. (1985); Proc. Natl. Acad. Sci. U.S.A. 82, 6507–6511) it appears that several active PAF forms may be produced: Form 1 PAF (see also Example 7) may be produced from this DNA by initiation of translation at some point 5' to the sequence AGTMAA . . . . and subsequent post-translational cleavage of the AG bond by a process yet to be established. In addition, a form 3 PAF may be produced by initiation of translation at the MAA sequence, since this is a consensus initiation site (M. Kozak, Microbiol. Rev. 1983, Vol. 47, 1–45) with optional proteolytic removal of the Methionine. Form 3 PAF may also be produced by initiation at other functional initiation sites. These sites are readily discernable to one of ordinary skill in the art, particularly in light of the teachings contained herein. In addition, post-translational processing of the initial translation product may then follow, although such processing is not required. Form 2 PAF may be produced from form 1 or form 3 of PAF by an as yet unknown process leading to blockage of the free amino group at the N-terminus.

EXAMPLE 9

Expression of PAF

The principle of the expression of PAF is as follows. A 1.1 kb EcoRI fragment isolated from the lambda gt10 clone can be subcloned into the plasmid pUC9. That fragment contains all of the PAF coding sequence. Two smaller fragments from this subclone are of utility in constructing expression systems. One is a 367 bp AvaI to BamHI fragment which contains amino acid residues 17 through 137 of the PAF coding sequence, counting the GTMAA residues of the placental form 1 protein as 1-5 The other is a 405 bp NcoI to BamHI fragment which contains amino acid residues 4 through 137 of the PAF coding sequence. Synthetic adaptors can then be attached to complete the coding sequence at both ends of these restriction fragments to provide translational initiation, termination, or coupling sequences and to supply the sequences necessary for attachment to the appropriate expression vector.

PAF isolated from human placenta contains a sequence which starts with GTMAA. The cNDA clones isolated from SK-Hep-1 cells indicated that other forms of PAF may be synthesized starting at least 100 amino acides upstream of the GTMAA sequence, or starting with MAA. The placental form was chosen for expression in yeast (*S. cerevisiae*) and bacteria (*E. coli*). The potential SK-Hep-1 form and any other amino terminally truncated form can be expressed by minor modifications of the procedures described below that should be obvious to one skilled in the art. They consist of altering the synthetic adaptors used to attach the amino terminal end of the cDNA fragment (either the NcoI site or the AvaI site) to the expression vectors. Alternatively, plasmids expressing truncated forms can be constructed from the GTMAA forms described below by oligonucleotide-directed deletion mutagenesis (as described by M. Inouye, K. Nakamura, S. Inouye, and Y. Masui in "Nucleic Research Future Development," K. Mizobuci, I. Watanabe, and J. D. Watson, eds., Academic Press, New York, pp. 419–436, 1983, specifically incorporated herein by reference).

Adaptors

The following adaptors were synthesized on an Applied Biosystems DNA synthesizer and gel purified. The 5' ends were phosphorylated with T4polynucleotide kinase (Pharmacia). Pairs of complementary oligonucleotides were annealed as follows to form the double stranded adaptor. Equimolar amounts of each oligonucleotide were added to a solution of 50 mM NaCl, 10 mM Tris pH 7.5 and 1 mM EDTA. This solution was heated in a boiling water bath. The water bath was then removed from heat and allowed to cool to ambient temperature over two hours. The following is a list and description of the adaptors used.

PAF Adaptors for attachment to the α-factor promoter of yeast

NH3 terminal adaptors:
1, GT Form
HindIII    #1A  5' AGCTTGGATAAGAGAGGGAC 3'        To NcoI
site of                                            site of PAF
-factor    #1B  3'   ACCTATTCTCTCCCTGGTAC 5'

2, COOH terminal adaptor:
BamHI   #2A  5' GATCTAAAAACAGGACCTGGGCAGAAAGCTATACTTTTTCTTCCAATGTCTGCTAAGAGCTGATAAGCC 3'    To SalI
site of                                                                                      site of
PAF     #2B  3'        ATTTTGTCCTGGACCCGTCTTTCGATATGAAAAAGAAGGTTAGAGACGATTCTGACTATTCGGAGCT 5'  α-factor Adaptors for Expression in E. coli For cytoplasmic production
3 NH3 terminal adaptors for GT form
       PvuI site  5'   CAAGGAGAAATAAATGGGACCATGGCAGCCGGGAGCATCACCACGCTGCCGCCTTGC 3'              AvaI site
b   of Omp      3' TAGTTCCTCTTTATTTACCCTGGTACCGTCGGCCCTCGTAGTGGTGCGACGGCGGAACGGGCT 5'           of PGF Omp EcoRI to PvuI fragment
5' AATTCGATATCTCGTTGGAGATATTCATGACGTATTTGGATGATAACGAGGCGCAAAAAATGAAAAAGACAGTATCGCGAT 3'
3'      GCTATAGAGCAACCTCTATAAGTACTGCATAAACCTACTATTGCTCCGCGTTTTTTACTTTTTCTGTCGATAGCGC 5'

4, COOH terminal adaptor;
BamHI   #4A  5' GATCTAAAAACAGGACCTGGGCAGAAAGCTATACTTTTTCTTCCAATGTCTGCTAAGAGCTGACTGCA 3'    to PstI
site of                                                                                    site of pCJ-1
PAF     #4B  3'      ATTTTGTCCTGGACCCGTCTTTCGATATGAAAAAGAAGGTTACAGACGATTCTCGACTG 5'

Adaptors for Secretion of PAF in E. coli using the Omp leader sequence

NH3 terminal adaptors
5 GT form:
5a  5' CCGGGACCATGGCAGCCGGGAGCATCACCACGCTGCCGCCTTGC 3'                     To AvaI site of PAF
5b  3' GGCCCTGGTACCGTCGGCCCTCGTAGTGGTGCGACGGCGGAACGGGCT 5'

Both of these adaptors will be ligated to the Omp leader described below.
5' AATTCGATATCTCGTTGGAGATATTCATGACGTATTTGGATGATAACGAGGCGCAAAAAATGAAAAAGACAGTATCGCGATCGCAGTGGC
3'      GCTATAGAGCAACCTCTATAAGTACTGCATAAACCTACTATTGCTCCGCGTTTTTTACTTTTTCTGTCGATAGCGCTAGCGTCACCG

ACTGGCTGGTTTCGCTACCGTAGCGCAGG 3'
TGACCGACCAAAGCGATGGCATCGCGTCC 5'

4, COOH terminal adaptor:
BamHI   #4A  5' GATCTAAAAACAGGACCTGGGCAGAAAGCTATACTTTTTCTTCCAATGTCTGCTAAGAGCTGACTGCA 3'    To PstI
site of                                                                                    site of pCJ-1
PAF     #4B  3'      ATTTTGTCCTGGACCCGTCTTTCGATATGAAAAAGAAGGTTACAGACGATTCTCGACTG 5'

```
                                                176                                                           206
GGG ACC ATG GCA GCC GGG AGC ATC ACC ACG CTG CCC GCC TTG CCC GAG GAT GGC GGC AGC
Gly Thr Met Ala Ala Gly Ser Ile Thr Thr Leu Pro Ala Leu Pro Glu Asp Gly Gly Ser
                                                236                                                           266
GGC GCC TTC CCG CCC GGC CAC TTC AAG GAC CCC AAG CGG CTG TAC TGC AAA AAC GGG GGC
Gly Ala Phe Pro Pro Gly His Phe Lys Asp Pro Lys Arg Leu Tyr Cys Lys Asn Gly Gly
                                                296                                                           326
TTC TTC CTG CGC ATC CAC CCC GAC GGC CGA GTT GAC GGG GTC CGG GAG AAG AGC GAC CCT
Phe Phe Leu Arg Ile His Pro Asp Gly Arg Val Asp Gly Val Arg Glu Lys Ser Asp Pro
                                                356                                                           386
CAC ATC AAG CTA CAA CTT CAA GCA GAA GAG AGA GGA GTT GTG TCT ATC AAA GGA GTG TGT
His Ile Lys Leu Gln Leu Gln Ala Glu Glu Arg Gly Val Val Ser Ile Lys Gly Val Cys
                                                416                                                           446
GCT AAC CGT TAC CTG GCT ATG AAG GAA GAT GGA AGA TTA CTG GCT TCT AAA TGT GTT ACG
Ala Asn Arg Tyr Leu Ala Met Lys Glu Asp Gly Arg Leu Leu Ala Ser Lys Cys Val Thr
                                                476                                                           506
GAT GAG TGT TTC TTT TTT GAA CGA TTG GAA TCT AAT AAC TAC AAT ACT TAC CGG TCA AGG
Asp Glu Cys Phe Phe Phe Glu Arg Leu Glu Ser Asn Asn Tyr Asn Thr Tyr Arg Ser Arg
                                                536                                                           566
AAA TAC ACC AGT TGG TAT GTG GCA CTG AAA CGA ACT GGG CAG TAT AAA CTT GGA TCC AAA
Lys Tyr Thr Ser Trp Tyr Val Ala Leu Lys Arg Thr Gly Gln Tyr Lys Leu Gly Ser Lys
                                                596
ACA GGA CCT GGG CAG AAA GCT ATA CTT TTT CTT CCA ATG TCT GCT AAG AGC TGA
Thr Gly Pro Gly Gln Lys Ala Ile Leu Phe Leu Pro Met Ser Ala Lys Ser End
```

EXAMPLE 9

Construction of Yeast Expression Plasmids

A plasmid, pGS185, derived from pUC 8 but lacking the restriction sites in the polylinker from the Hind III site to the SmaI site, was constructed by digesting pUC 8 with Hind III, ligated it to a Hind III/SmaI adaptor (Amersham, Cat. No. DA1006) which does not reconstruct the Hind III site, digesting with SmaI and ligating in dilute solution (1 ng/ml) followed by transformation of E. coli JM 83. The correct plasmid, was identified by digesting plasmid DNA isolated from transformants with EcoRI, SmaI or Hind III. A transformant containing a plasmid that lacked the Hind III site but contained the EcoRI site and SmaI site was identified in this manner.

An EcoRI fragment containing yeast MFα1 gene was purified by gel electrophoresis from the plasmid pCY17 as described by J. Kurgan and I. Herskowitz in Cell 30:933 (1982) and ligated into EcoRI cut pGS185. This ligation mixture was used to transform E. coli HB101, selecting for ampicillin resistance. Plasmid DNA was isolated from transformants and the presence of the correct insert confirmed by digests of the DNA with EcoRI. This is plasmid pGS285.

Plasmid pGS285 was digested to completion with Hind III and religated under dilute conditions (1 ng/ml) to eliminate three of the four internal Hind III sites in the MRα1 gene as noted by Kurjan and Herskowitz, ibid. The correct construct was selected as described above. This is plasmid pGS385.

For site-directed mutagenesis, the MFα1 gene was removed from pGS by digestion with EcoRI, gel purified (1.5 Kb) and ligated to EcoRI digested M13 mp18 RF. The ligation mixture was used to transform E. coli 71-18 and clones containing the MFα1 gene in the correct orientation were identified by hybridization to the [$^{32}$p] labeled MFα1 gene. The MFα1 sequence was changed from GTA TCT TTG GAT AAA AGA to GTA AGC TTG GAT AAA AGA using standard site directed in vitro mutagenesis methods described by Zoller and Smith (Methods in Enzymology, Vol. 100, 1983, Academic Press, Inc., p. 468). The sequence of the mutant α-factor gene, MFα-H, was confirmed by dideoxy sequencing.

The MFα-H gene was removed by digesting the RF form of the M13 mp18 clone with EcoRI, gel-purifying the resulting 1.5 Kb EcoRI fragment by acrylamide gel electrophoresis and ligating it to EcoRI cut pGS185. The resulting ligation mixture was used to transform E. coli HB101 and colonies containing the plasmids with the MFα-H gene were identified by hybridization with $^{32}$p labeled 1.5 Kb EcoRI fragment containing the MFα-H gene. This plasmid is designated pGS286.

The PAF gene was inserted into pGS286 as follows. Adaptors #1 and #2 were ligated to the PAF NcoI/-BamHI fragment. The ligation mixture was electrophoresed on a polyacrylamide gel and PAF DNA with the attached adaptors identified by an increase in MW. This correctly adapted DNA fragment was eluted from the gel, and was ligated to Hind III/SalI digested pGS286. E. coli HB101 was transformed with the ligation mixture and ampicillin resistant colonies were selected. Transformants containing plasmids with the correct insert were identified by hybridization with adaptor 1A and 2A, radio labelled by incubation with [γ-$^{32}$p]ATP and T4 polynucleotide kinase. A plasmid constructed and isolated in this manner has been designated pGS286-PAF. This plasmid contains the MFαH gene fused, in frame, to the PAF gene at the Hind III site in the "pre-pro" region of the MFαH gene. Such constructs, when placed in yeast, have been demonstrated to direct the synthesis, processing and secretion of heterologous proteins as shown by A. J. Brake et al., 1981 (PNAS (U.S.A.) 81:4642).

The EcoRI fragment containing the fusion of the MF H gene and PAF is pGS286-PAF. This fragment was isolated by digestion with EcoRI and polyacrylamide gel electrophoresis. It was made blunt ended with T4 DNA polymerase and PstI adaptors (Pharmacia) were attached with T4 DNA ligase. The fragment was then ligated into PstI digested vector pCl/1 (A. J. Brake et al. 1981) (PNAS, (U.S.A.) 81:4642) and *E. coli* HB101 transformed with the ligation mix and TET$^r$ colonies were selected. Correct constructs were identified by hybridization to the PAF gene. The plasmid was introduced into *S. cerevisiae* DBY 746 (Yeast Genetic Stock Center, Berkeley, Calif.), with the two micron DNA plasmid deleted as described by Toh-E and Wickner (Journal of Bacteriology, 145, 1981, 1421–1424), by standard transformation protocols. Transformants expressing PAF were selected by their reactivity with affinity purified anti PAF IgG.

EXAMPLE 10

Periplasmic Secretion in *E. coli*

To regulate the expression of PAF in a form suitable for export to the periplasm of *E. coli*, the following regulatory elements were used: a tac promoter on plasmid pCJ-1 for initiation of transcription at high levels; a lac operator on plasmid pCJ-1 for transcription regulation; a lac repressor (lac I$^q$), encoded on the chromosone of *E. coli* strain JM107. To facilitate periplasmic export of PAF, DNA coding for the Omp A leader peptide was attached to the DNA coding for PAF in such a way that the C-terminal Ala of this peptide will be fused to the N-terminal Gly of PAF form 1 in such a way that the Ala-Gly bond of the initial product will be cleaved by the *E. coli* leader peptidase to yield the mature PAF.

The *E. coli* secretion vector was constructed as follows. Adaptors #5 and #4 were ligated to the PAF AvaI/BamHI fragment. DNA of the correct size was eluted from a polyacrylamide gel and ligated to the Omp A leader DNA and EcoRI/PstI digested M13 mp19 RF. *E. coli* JM-107 were transformed with the ligation mix. Transformants containing the PAF gene were detected by restriction mapping and the sequence of the construct was confirmed by dideoxy sequencing. The EcoRI/PstI fragment containing the PAF gene was isolated from the RF DNA by restriction with EcoRI and PstI and elution from a polyacrylamide gel. This was ligated into EcoRI/PstI digested pCJ-1 and *E. coli* JM107 were transformed with the ligation mixture. Colonies producing PAF were selected by growth on Tet plates and immunoscreening with affinity purified anti-PAF IgG.

EXAMPLE 11

Cytoplasmic Expression in *E. coli*

To regulate the expression of PAF in a form such that the PAF remains in the *E. coli* cytoplasm, the following operational elements were used: the tac promoter on plasmid pCJ-1; the lac operator of the plasmid pCJ-1 and the lac repressor (lac I$^q$) on the chromosone of *E. coli* strain JM107; a consensus Shine-Dalgarno sequence; and, to initiate a high level of translation, a fragment of the Omp A leader peptide to be used as a translational coupler. The translational coupling sequence comprises the DNA coding for the translation initiation region of the OMP A gene, the first eight amino acids of the OMP A leader peptide, the consensus Shine-Dalgarno sequence described above and a translational terminator. The translational coupling sequence is to be inserted between the lac operator and the translation initiation site of the PAF gene, overlapping the latter. (The features of the translational coupler are incorporated on the DNA sequence shown with the adaptors for secreted expression in *E. coil*.)

The PAF gene was incorporated into the pCJ-1 plasmid with the translational coupler as follows. Adaptor #3 and the OMP A translational coupler were attached to the PAF AvaI/PstI fragment from the M13 mp19 construct described in Example 10. This fragment was purified from a polyacrylamide gel. This fragment was then ligated into EcoRI/PstI digested M13 mp19 RF and the ligation mix used to transform *E. coli* JM 107 cells. Plaques containing the PAF gene fusion were chosen by restriction mapping. The sequence of the construct was then confirmed by dideoxy sequencing. The EcoRI/PstI fragment containing the PAF gene fusion was eluted from a polyacrylamide gel and ligated into EcoRI/PstI digested pCJ-1 and *E. coli* JM107 cells were transformed with the ligation mix. Colonies showing tetracycline resistance were selected and PAF production was confirmed by immunoscreening with affinity purified anti-PAF IgG.

It will be apparent to those skilled in the art that various modifications and variations can be made to the processes and products of the present invention. Thus, it is intended that the present invention cover these modifications and variations of this invention provided they come within the scope of the appended claims and their equivalents.

EXAMPLE 12

Cytoplasmic Expression in *E. coli*

The M13 and mp19 secretion construct described in Example 10 was digested with NruI and NcoI and the large fragment was eluted from a gel. Adaptor #6 was then ligated into the NruI/NcoI cut DNA. *E. coli* strain JM107 was transformed with the ligation mix. Plaques containing the PAF gene fusion were confirmed by dideoxy sequencing. The EcoRI/PstI fragment containing the PAF gene fusion was eluted from a polyacrylamide gel and ligated into EcoRI/PstI digested pCJ-1 and *E. coli* JM107 cells were transformed with the ligation mix. Colonies showing tetracycline resistance were selected and PAF production was confirmed by immunoscreening with affinity purified anti-PAF IgG.

```
Adaptor #6
#6a NruI site 5' CGATCAAGGAGAAATAAATGGGGAC     3' To NcoI
#6B OF Omp 3' GCTAGTTCCTCTTTATTTACCCCTGGTAC 5' site of PAF
```

EXAMPLE 13

Identification of mRNA

Total RNA was isolated from the following cell lines: SK HEP-1 human hepatoma cells, human embryonic lung (HEL) cells, RPMI 7272 human melanoma cells and mouse sarcoma 180 cells. Poly A plus minus messenger RNA (mRNA) was then isolated using oligo (DT) cellulose chromatography. Fifteen micrograms of poly A plus minus RNA from each of the above cell lines was separated by electrophoresis on a 1.25 percent agarose/formaldehyde gel. These RNAs were transferred to a zeta-probe membrane. A cDNA probe to human basic FGF from SK HEP-1 human hepatoma cells (FGF15, the EcoRI insert) was labeled with ³²P-DCTP by the NICK translation procedure to a specific activity of $8.64 \times 10^8$ cpm/ug. Hybridization of the ³²P-BFGF cDNA probe to the transferred RNA was carried out in 50 percent formamide, 6X SSC, 2X Denhardt's solution, 1 percent SDS, 0.05 percent sodium pyrophosphate and 175 ug/ml tRNA for 16 hours at 42° C. The zeta-probe membrane was then washed in 1 liter each of 0.5X SSC/1 percent SDS, 0.2X SSC/1 percent SDS, 0.1X SSC/1 percent SDS for 15 minutes at 65° C. and in 0.1X SSC/1 percent SDS for 15 minutes at 70° C. The membrane was then dried and autoradiography carried out for 1 and 3 days at −80° C. SK HEP-1 cells, HEL cells and RPMI 7272 cells each contained four species of RNA having sizes of 8.0 KB, 4.3 KB, 2.3 KB and 1.0 KB which hybridized to the cDNA probe described above. The cDNA probe did not hybridize to any RNA species from mouse sarcoma 180 cells.

What is claimed is:

1. An isolated DNA sequence encoding an angiogenic factor protein consisting of a single-polypeptide-chain protein having at least one active site possessing mitotic and chemotactic activity and the ability to stimulate protease synthesis, wherein said protein consists of the amino acid sequence:

G—T—M—A—A—G—S—I—T—T—L—P—A—L—P—E—D—
—G—G—S—G—A—F—P—P—G—H—F—K—D—P—K—
—R—L—Y—C—K—N—G—G—F—F—L—R—I—H—P—D—
—G—R—V—D—G—V—R—E—K—S—D—P—H—I—K—L—
—Q—A—E—E—R—G—V—V—S—I—K—G—V—C—A—N—
—R—Y—L—A—M—K—E—D—G—R—L—L—A—S—K—C—
—V—T—D—E—C—F—F—F—E—R—L—E—S—N—N—Y—
—N—T—Y—R—S—R—K—Y—T—S—W—Y—V—A—L—K—
—R—T—G—Q—Y—K—L—G—S—K—T—G—P—G—Q—K—
—A—I—L—F—L—P—M—S—A—K—S.

* * * * *

UNITED STATES PATENT AND TRADEMARK OFFICE
CERTIFICATE OF CORRECTION

PATENT NO. : 5,026,839  Page 1 of 2

DATED : June 25, 1991

INVENTOR(S) : David Moscatelli et al.

It is certified that error appears in the above-identified patent and that said Letters Patent is hereby corrected as shown below:

ON THE TITLE PAGE:

Under "Related U.S. Application Data", line 3, delete "abandoned" and substitute therefor --issued as U.S. Patent No. 4,994,559--.

At column 3, beginning at line 51, and at column 6, beginning at line 24, and at column 15, beginning at line 26, and in claim 1, column 28, beginning at line 9.

UNITED STATES PATENT AND TRADEMARK OFFICE
CERTIFICATE OF CORRECTION

PATENT NO. : 5,026,839

DATED : June 25, 1991

INVENTOR(S) : David Moscatelli et al

It is certified that error appears in the above-identified patent and that said Letters Patent is hereby corrected as shown below:

Abstract, beginning at line 7, delete the entire amino acid sequence and substitute therefor:

--G-T-M-A-A-G-S-I-T-T-L-P-A-L-P-E-D-G-G-S-
G-A-F-P-P-G-H-F-K-D-P-K-R-L-Y-C-K-N-G-G-
F-F-L-R-I-H-P-D-G-R-V-D-G-V-R-E-K-S-D-P-
H-I-K-L-Q-L-Q-A-E-E-R-G-V-V-S-I-K-G-V-C-
A-N-R-Y-L-A-M-K-E-D-G-R-L-L-A-S-K-C-V-T-
D-E-C-F-F-F-E-R-L-E-S-N-N-Y-N-T-Y-R-S-R-
K-Y-T-S-W-Y-V-A-L-K-R-T-G-Q-Y-K-L-G-S-K-
T-G-P-G-Q-K-A-I-L-F-L-P-M-S-A-K-S.--

Signed and Sealed this

Tenth Day of November, 1992

Attest:

DOUGLAS B. COMER

Attesting Officer

Acting Commissioner of Patents and Trademarks